(12) United States Patent
Mathiaparanam et al.

(10) Patent No.: US 6,323,376 B1
(45) Date of Patent: Nov. 27, 2001

(54) PROCESS FOR PREPARING ALKOXY OR ARYLMETHOXY AROXYETHANES

(75) Inventors: Ponnampalam Mathiaparanam, Appleton; Debra Arlene Berggren, Kimberly, both of WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

(21) Appl. No.: 09/775,027

(22) Filed: Feb. 1, 2001

Related U.S. Application Data
(60) Provisional application No. 60/183,275, filed on Feb. 17, 2000.

(51) Int. Cl.$^7$ .............................. C07C 41/26; C07C 43/20
(52) U.S. Cl. ........................... 568/626; 568/631; 568/632; 568/633
(58) Field of Search ............................. 568/626, 631, 568/632, 633, 634

(56) References Cited

U.S. PATENT DOCUMENTS

| | | | |
|---|---|---|---|
| 2,172,606 | 9/1939 | Butler et al. | 260/456 |
| 2,987,555 | 6/1961 | Davis | 260/613 |
| 4,341,905 | 7/1982 | Strege | 568/45 |
| 5,179,068 | 1/1993 | Goto | 503/209 |

OTHER PUBLICATIONS

C.L. Butler and A.G. Renfrew, Hydroxyalkyl Ethers of Basic Phenols. The Antipneumococcic Activity of Some 8–Quinolyl Ethers, Journal American Chemical Society 60, 1582 (1938).

J.S. Bradshaw, B.A. Jones, J.S. Bebhard, Formation of Ethers by the Reductive Desulfurization of Thiono Esters, Journal Organic Chemistry, 48, 1127 (1983).

E.M. Van Dunzee, H. Adkins, Hydrogenation and Hydrogenolysis of Ethers, Journal American Chemical Society, 57, 147 (1935).

C. Berggardh, Spjalkning av glykoletrar med acetyl bromid, Finska Kemistsamf.Medd, 42, 76 (1933).

*Primary Examiner*—Johann Richter
*Assistant Examiner*—Sikarl A. Witherspoon

(74) *Attorney, Agent, or Firm*—Benjamin Mieliulis

(57) ABSTRACT

The present invention is a novel process, with or without solvent, for manufacture of compounds of the formula

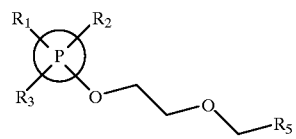

wherein P is selected from phenyl and naphthyl;

wherein $R_1$ and $R_2$ and $R_3$ are each independently selected from hydrogen, alkyl, alkoxy, aryl, aralkyl, aralkoxy, halogen, alkoxyalkoxy, and aralkoxyalkoxy; wherein $R_5$ is selected from substituted or unsubstituted phenyl, and substituted or unsubstituted naphthyl, the substituents being each independently selected from alkyl ($C_1$–$C_8$), alkoxy ($C_1$–$C_8$), aroxy, aralkoxy ($C_1$–$C_8$) and halogen. The process comprises reacting substituted phenols or naphthols of the formula

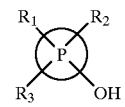

with ethylene carbonate in the presence of a first catalyst selected from metal halide, quarternary ammonium halide and quarternary phosphonium halide thereby forming an intermediate of the formula

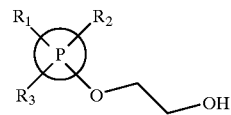

then reacting the intermediate with a first compound selected from alkyl or aralkylhalide, alkyl or aralkyl sulfate, and alkyl or aralkyl sulfonate together with a metal hydroxide in the presence of a second catalyst, the second catalyst selected from quarternary ammonium salt or quarternary phosphonium salt.

12 Claims, No Drawings

PROCESS FOR PREPARING ALKOXY OR ARYLMETHOXY AROXYETHANES

This application under 35 USC §111(a) claims benefit per 35 USC §119(e) to application Ser. No. 60/183,275 filed Feb. 17, 2000 as a provisional application per 35 USC §111(b).

BACKGROUND OF THE INVENTION

1. Field of the Invention

This invention relates to alkoxy or arylmethoxy ethanes. This invention particularly concerns a process for preparation of such compounds. More particularly, the invention teaches a novel process for preparation of 2-alkoxy (or 2-arylmethoxy)-1-aroxyethanes, a class of compounds useful in a variety of diverse applications such as improved sensitizers or modifiers for thermal sensitive papers and as dispersants, emollients, and texture enhancing agents in cosmetics and lotions.

2. Description of Related Art

There are several methods described in the literature for preparing 1-benzyloxy-2-phenoxyethane represented by the structure A:

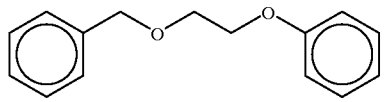

(A)

C. Berggardh [Finska Kemistsamf.Medd., 42, 76 (1933)] and E. M. Van Duzee and H. Atkins [J. Amer. Chem. Soc., 57, 147 (1935)] prepared (A) by reacting sodium 2-phenoxyethoxide with benzyl chloride. Also, C. L. Butler and A. G. Renfrew [J. Amer. Chem. Soc., 60, 1582 (1938)] and C. L. Butler and L. H. Cretcher [U.S. Pat. No. 2,172,606 (1939)] obtained (A) by treating 2-benzyloxyethyl p-toluenesulfonate with potassium phenoxide. These two methods require the preparation of one or both starting materials in a separate step and involves the use of either potassium or sodium metal that are expensive and difficult to handle in scale up operations. J. S. Bradshaw, B. A. Jones and J. S. Gebhard [J. Org. Chem., 48, 1127 (1983)] made (A) by reductive desulfurization of 2-phenoxyethyl thiobenzoate using Raney nickel. Again, the starting material thiobenzoate, prepared from not readily available 2-phenoxyethyl benzoate by thionation, makes this process not amenable to scale up. A. Goto [U.S. Pat. No. 5,179,068] described a method for preparing 1,4-bis (2-aroxyethoxymethyl) benzenes by reacting 2-phenoxyethanol with p-xylylene dichloride and aqueous sodium hydroxide using trioctylmethylammonium chloride as catalyst in toluene. Goto also, described a process for making 1,4-bis (2-aroxyethoxymethyl) benzenes in two steps starting from substituted phenol and ethylene carbonate. In the first step, the substituted phenol and ethylene carbonate were heated with catalytic amounts of potassium carbonate in chlorobenzene to generate the corresponding substituted phenoxyethanol. In the second step, the substituted phenoxyethanol was reacted with p-xylylene chloride and aqueous sodium hydroxide using trioctylmethylammonium chloride as catalyst in chlorobenzene. The success of this tandem two step process depends on the complete conversation of the substituted phenol to the corresponding substituted phenoxyethanol in the first step; otherwise, a mixture of inseparable products are formed, resulting in low yield of the desired product.

DETAILED DESCRIPTION

The present invention is a novel process for manufacturing 2-alkoxy (or 2-arylmethoxy)-1-aroxyethanes using a one-pot, two-step procedure. The novel process comprises reacting substituted or unsubstituted phenol (or naphthol) with ethylene carbonate in the presence of a first catalyst, with or without solvent, and reacting the product formed in the first step with alkyl or aralkyl halide (sulfate or sulfonate) and metal hydroxide in the presence of a second catalyst with or without solvent.

This invention teaches a process for preparing 2-alkoxy (or 2-arylmethoxy)-1-aroxyethanes. Particularly, this invention teaches a novel process for preparing 2-alkoxy (or 2-arylmethoxy)-1-aroxy-ethanes represented by the formula (I):

(I)

wherein P is selected from phenyl and naphthyl moieties.

Formula (IIA) depicts when P in the structure of Formula 1 is replaced by phenyl

(IIA)

Formula IIB depicts when P in the structure of Formula I is replaced by naphthyl.

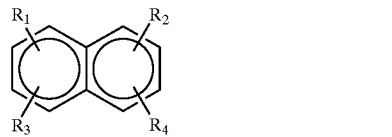

(IIB)

In each of formulas I, IIA and IIB the substituents $R_1$, $R_2$ and $R_3$ are independently hydrogen, alkyl, alkoxy, aryl, aralkyl, aralkoxy, halogen, alkoxyalkoxy and aralkoxyalkoxy; and $R_4$, is independently alkoxyethyl, alkoxyethoxy and aralkoxyethoxy.

In the substituents $R_1$, $R_2$, $R_3$ and $R_4$, the alkyl moieties in alkyl, alkoxy, aralkyl, aralkoxy, alkoxyalkyl, alkoxyalkoxy and aralkoxyalkoxy groups contain one through eight carbon atoms.

This invention teaches an improved process for manufacturing 2-alkoxy (or 2-arylmethoxy)-1-aroxyethanes (VIII) using a one-pot, two-step procedure from readily available materials. The process of the invention is diagrammed as follows:

Scheme 1

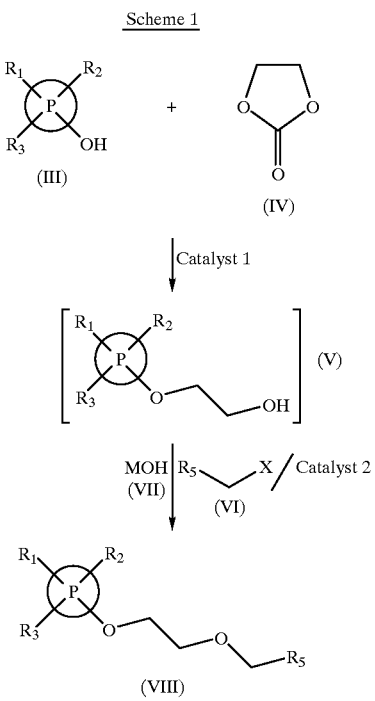

The substituents P, $R_1$, $R_2$ and $R_3$ are as defined previously. $R_5$ is either a substituted or unsubstituted phenyl or naphthyl group. The substituents on the phenyl or naphthyl groups include alkyl ($C_1$–$C_8$), alkoxy ($C_1$–$C_8$), aroxy, aralkoxy ($C_1$–$C_8$ alkyl) and halogen. For clarity "aralkoxy ($C_1$–$C_8$)" herein will refer to the alkyl moiety as having from one to eight carbons.

The process comprises reacting substituted or unsubstituted phenols (or naphthols) (III) with ethylene carbonate (IV) using catalyst 1 without a solvent and reacting the product formed (V) in the first step with alkyl or aralkyl halide (sulfate or sulfonate) (VI) and metal hydroxide in the presence of catalyst 2 with or without a solvent.

By heating the phenol (or naphthol) (III) with slight excess of ethylene carbonate and the catalyst 1 without solvent, the phenol (or naphthol) is completely converted to the corresponding 2-phenoxy (or 2-naphthoxy) ethanol (V). The reaction temperature may be selected from 50° C. to 200° C. depending on the phenol (or naphthol) used. Most of the phenols (or naphthols) react in the preferred temperature range from 140° C. to 160° C.

The catalyst 1 that is suitable for this reaction include metal halides, quarternary ammonium halides and quarternary phosphonium halides. Preferred catalysts include sodium chloride, sodium bromide, sodium iodide, potassium chloride, potassium bromide, potassium iodide, tetraethylammonium chloride, tetraethylammonium bromide, tetraethylammoniumiodide, tetrabutylammonium chloride, tetrabutylammonium bromide, tetrabutylammonium iodide, methyltrioctylammonium chloride (aliquat 336), tetraethylphosphonium chloride, tetraethylphosphonium bromide and tetraethylphosphonium iodide. Also, a combination of quarternary ammonium salt or quarternary phosphonium salt other than halides and metal halides can be used as catalyst 1.

The intermediate (V) was then mixed with alkyl or aralkyl halide (sulfate or sulfonate) (VI), metal hydroxide (VII) and catalyst 2, heated and stirred vigorously. Powdered metal hydroxide was used in the solvent free procedure. Aqueous solution (40–50%) of metal hydroxide was used with a solvent in the solvent procedure. Preferred metal hydroxides include sodium hydroxide and potassium hydroxide and the preferred solvents are aliphatic or aromatic hydrocarbons or chlorohydrocarbons. Catalyst 2 may be either quarternary ammonium salt or quarternary phosphonium salt. Preferred catalyst 2 are tetrabutylammonium hydrogen sulfate, tetrabutylammonium halide, tetraethylammonium halide, methyltrioctylammonium choride (also known as aliquat 336) and tetraethylphosphonium halide. The reaction temperature for the second step is dependent on the solvent used. The preferred temperature range is room temperature to 55° C. for low boiling point solvents and 50–100° C. for high boiling point solvents. For the solvent free procedure 90–100° C. temperature range is preferred.

By carrying out the step 1 of this process in excess of ethylene carbonate (IV), the phenol (or naphthol) (III) is completely converted to the corresponding 2-phenoxy (or 2-naphthoxy) ethanol (V). No solvent need be used (solvent being optional but preferably omitted in Step 1) and excess ethylene carbonate and lower boiling materials are removed under reduced pressure. This complete conversion is important; otherwise, a mixture of unwanted by products are obtained by reaction of (III) with (VI). This is one of the features of this tandem process.

In step 2, (V) is converted to (VIII) using either a solvent-free or a solvent procedure. In the solvent-free procedure, a solid liquid phase transfer catalysis reaction was selected because it gives complete conversion. Metal hydroxides should be finely powdered and the stirring should be vigorous to produce efficient conversion. In the solvent procedure, an aqueous solution of the metal hydroxide and a suitable solvent was used as in traditional phase transfer catalysis reaction. Here again, vigorous stirring is recommended for optimum conversion.

The solvent-free options and the one-pot process enable scale up for commercial production. Furthermore, by changing the phenol (or naphthol) (III) and alkyl or aralkyl halide (sulfate or sulfonate) (VI), a series of 2-alkoxy (2-arylmethoxy)-1-aryloxyethanes (VII) were prepared. Some of compounds (VII) prepared are listed below:

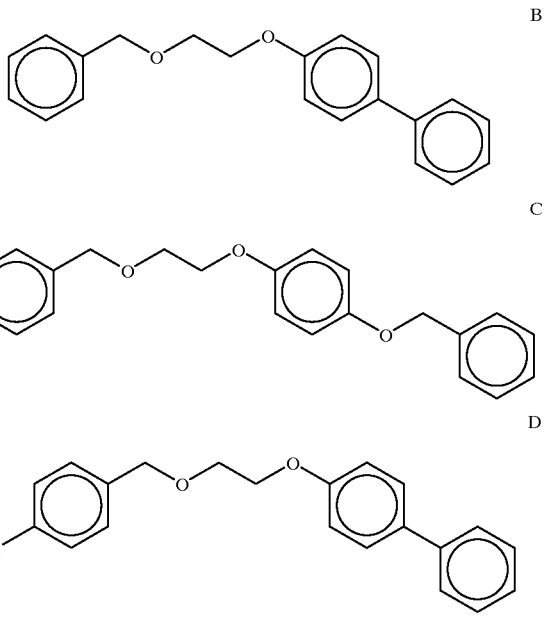

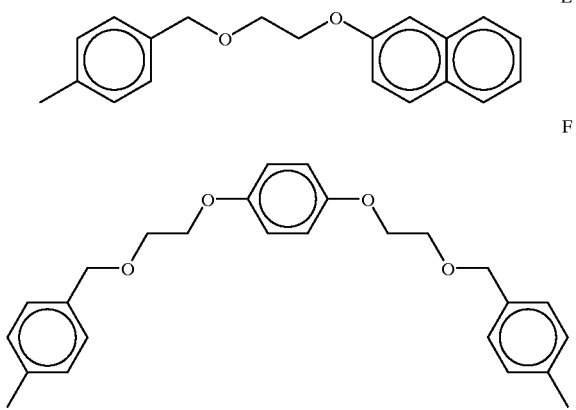

DESCRIPTION OF THE PREFERRED EMBODIMENTS

In the following examples, general procedures for preparing certain compounds listed above are described; the examples are not intended to be exhaustive and the moieties, as previously defined, are all eligible for use in any combination in preparing the compounds. Unless otherwise noted, all measurements, percentages and parts are by weight and in the metric system.

EXAMPLE 1

Preparation of 1-Benzyloxy-2-[4-(benzyloxy) phenoxy]ethane (Compound C) by Solvent-Free Reaction 4-Benzyloxyphenol (60.6 g, 0.3 mole), ethylene carbonate (32.0 g, 0.36 mole) and sodium chloride (4.0 g, 0.07 mole) were placed in a 500 ml, three-necked, round-bottom flask equipped with a mechanical stirrer and a reflux condenser. The reaction mixture was stirred and heated to 155° C. After 9 hours, the reaction mixture was cooled to 100° C. and most of the lower boiling materials were removed under reduced pressure. Then, tetrabutylammonium hydrogen sulfate (4.0 g, 0.012 mole) and finely powdered potassium hydroxide (28.0 g, 0.5 mole) were added to the reaction mixture and the vigorous stirring was continued. After five minutes, benzyl chloride (45.0 g, 0.36 mole) was added slowly with vigorous stirring. After four hours, toluene (200 ml) and water (60 ml) were added and stirring was continued for another ten minutes. The toluene layer was separated and the in aqueous layer was extracted twice with toluene. The in toluene layers were combined and washed with water, dried and concentrated. The residue was recrystallized from methanol. Yield: 82.6 g (82%), White solid, M.P.: 71–73° C.

EXAMPLE 2

Preparation of 1-Benzyloxy-2-[4-(benzyloxy)phenoxy] ethane (Compound C)

4-Benzyloxyphenol (60.6 g, 0.3 mole), ethylene carbonate (32.0 g, 0.36 mole) and sodium iodide (2.25 g, 0.015 mole) were placed in a 500 ml, three-necked, round-bottom flask equipped with a mechanical stirrer and a reflux condenser. The reaction mixture was stirred and heated at 155° C. After 5 hours, the reaction mixture was cooled to 110° C. and most of the lower boiling materials were removed under reduced pressure. Then, tetrabutylammonium hydrogen sulfate (4.0 g, 0.12 mole), benzyl chloride (45.0 g, 0.35 mole), toluene (200 ml) and sodium hydroxide (20.0 g, 0.5 mole/40 ml of water) were added to the reaction mixture and the vigorous stirring was continued while the reaction mixture temperature was lowered to 90° C. After overnight at this temperature, the reaction mixture was cooled to room temperature and transferred to a separatory funnel. The toluene layer was separated and the aqueous layer was extracted twice with toluene. Toluene extracts were combined, washed with water, dried, treated with Norit A and filtered. The filtrated was passed through a short column of silica gel and eluted with toluene. Fractions containing the product were collected, combined and concentrated. The residue was recrystallized from methanol. Yield: 72.6 g (72%), White solid, M.P.: 71–73° C.

EXAMPLE 3

Preparation of 1-(4-Chlorobenzyloxy)-2-(4-phenylphenoxy)ethane (Compound D) by Solvent-Free Reaction 4-Phenylphenol (34.0 g, 0.2 mole), ethylene carbonate (20.0 g, 0.227 mole) and tetrabutylammonium bromide (6.5 g, 0.02 mole) were heated to 155° C. with stirring in a three-necked, round-bottom flask equipped with a mechanical stirrer and a reflux condenser. After 5 hours, the reaction mixture was cooled to 110° C., most of the lower boiling materials were removed under reduced pressure. Finely powdered potassium hydroxide (17.0 g, 0.3 mole) was added and the reaction mixture was stirred for 5 minutes. Then, 4-chloro-benzyl chloride (35.0 g, 0.217 mole) was added and the reaction was kept at 110° C. with vigorous stirring. After 4 hours, toluene (250 ml) was added and the reaction mixture was cooled to 60° C. Water (100 ml) was added and stirring continued. Toluene layer was separated and the aqueous layer was extracted twice with warm toluene. The toluene extracts were combined, washed with water, dried and concentrated. The residue was recrystallized from toluene/methanol. Yield: 55.8 g (82%), white solid, M.P.: 85–87° C.

We claim:

1. A novel process for manufacture of compounds of the formula

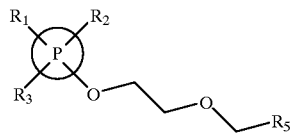

wherein P is selected from phenyl and naphthyl;

wherein $R_1$, $R_2$ and $R_3$ are each independently selected from the group consisting of hydrogen, alkyl, alkoxy, aryl, aralkyl, aralkoxy, halogen, alkoxyalkoxy, and aralkoxyalkoxy;

wherein $R_5$ is selected from substituted or unsubstituted phenyl, and substituted or unsubstituted naphthyl, the substituents being each independently selected from alkyl ($C_1$–$C_8$), alkoxy ($C_1$–$C_8$), aroxy, aralkoxy and halogen;

the process comprising reacting substituted or unsubstituted phenols or naphthols of the formula

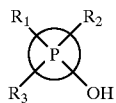

with ethylene carbonate in the presence of a first catalyst selected from the group consisting of metal halide, quarternary ammonium halide and quarternary phosphonium halide thereby forming an intermediate of the formula

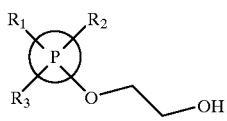

reacting the intermediate with a first compound selected from the group consisting of alkyl halide, aralkyl halide, alkyl sulfate, aralkyl sulfate, alkyl sulfonate and aralkyl sulfonate together with a metal hydroxide in the presence of a second catalyst, the second catalyst selected from quarternary ammonium salt or quarternary phosphonium salt.

2. The process according to claim 1 wherein the first catalyst is selected from the group consisting of sodium chloride, sodium bromide, sodium iodide, potassium chloride, potassium bromide, potassium iodide, tetraethylammonium chloride, tetraethylammonium bromide, tetraethylammoniumiodide, tetrabutylammonium chloride, tetrabutylammonium bromide, tetrabutylammonium iodide, methyltrioctylammonium chloride, tetraethylphosphonium bromide, and tetraethylphosphonium iodide.

3. The process according to claim 1 wherein the second catalyst is selected from the group consisting of tetrabutylammonium hydrogen sulfate, tetrabutylammonium halide, tetraethylammonium halide, methyltrioctylammonium chloride, and tetraethylphosphonium halide.

4. The process according to claim 1 wherein the reaction of the intermediate is carried out in a solvent selected from the group consisting of aliphatic hydrocarbons, aromatic hydrocarbons and chlorohydrocarbons.

5. A novel process for manufacture of compounds of the formula

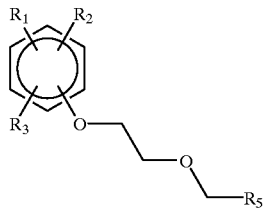

wherein $R_1$, $R_2$ and $R_3$ are each independently selected from the group consisting of hydrogen, alkyl, alkoxy, aryl, aralkyl, aralkoxy, halogen, alkoxyalkoxy, and aralkoxyalkoxy;

wherein $R_5$ is selected from substituted or unsubstituted phenyl, the substituents being each independently selected from alkyl ($C_1$–$C_8$), alkoxy ($C_1$–$C_8$), aroxy, aralkoxy and halogen;

the process comprising reacting substituted or unsubstituted phenols of the formula

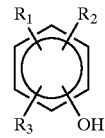

with ethylene carbonate in the presence of a first catalyst selected from the group consisting of metal halide, quarternary ammonium halide and quarternary phosphonium halide thereby forming an intermediate of the formula

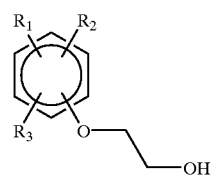

reacting the intermediate with a first compound selected from the group consisting of alkyl halide, aralkyl halide, alkyl sulfate, aralkyl sulfate, alkyl sulfonate and aralkyl sulfonate together with a metal hydroxide in the presence of a second catalyst, the second catalyst selected from quarternary ammonium salt or quarternary phosphonium salt.

6. The process according to claim 5 wherein the first catalyst is selected from the group consisting of sodium chloride, sodium bromide, sodium iodide, potassium chloride, potassium bromide, potassium iodide, tetraethylammonium chloride, tetraethylammonium bromide, tetraethylammoniumiodide, tetrabutylammonium chloride, tetrabutylammonium bromide, tetrabutylammonium iodide, methyltrioctylammonium chloride, tetraethylphosphonium bromide, and tetraethylphosphonium iodide.

7. The process according to claim 5 wherein the second catalyst is selected from the group consisting of tetrabutylammonium hydrogen sulfate, tetrabutylammonium halide, tetraethylammonium halide, methyltrioctylammonium chloride and tetraethylphosphonium halide.

8. The process according to claim 5 wherein the reaction of the intermediate is carried out in a solvent selected from the group consisting of aliphatic hydrocarbons, aromatic hydrocarbons and chlorohydrocarbons.

9. A novel process for manufacture of compounds of the formula

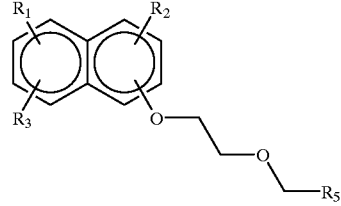

wherein $R_1$, $R_2$ and $R_3$ are each independently selected from the group consisting of hydrogen, alkyl, alkoxy, aryl, aralkyl, aralkoxy, halogen, alkoxyalkoxy, and aralkoxyalkoxy;

wherein $R_5$ is selected from substituted or unsubstituted naphthyl, the substituents being each independently selected from alkyl ($C_1$–$C_8$), alkoxy ($C_1$–$C_8$), aroxy, aralkoxy ($C_1$–$C_8$) and halogen; the process comprising reacting substituted or unsubstituted naphthols of the formula

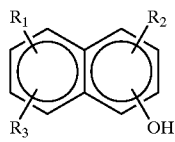

with ethylene carbonate in the presence of a first catalyst selected from the group consisting of metal halide, quarternary ammonium halide and quarternary phosphonium halide, thereby forming an intermediate of the formula

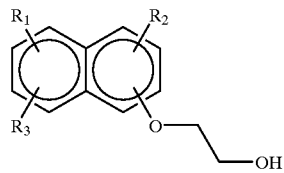

reacting the intermediate with a first compound selected from the group consisting of alkyl halide, aralkyl halide, alkyl sulfate, aralkyl sulfate, alkyl sulfonate and aralkyl sulfonate together with a metal hydroxide in the presence of a second catalyst, the second catalyst selected from quarternary ammonium salt or quarternary phosphonium salt.

10. The process according to claim 9 wherein the first catalyst is selected from the group consisting of sodium chloride, sodium bromide, sodium iodide, potassium chloride, potassium bromide, potassium iodide, tetraethylammonium chloride, tetraethylammonium bromide, tetraethylammoniumiodide, tetrabutylammonium chloride, tetrabutylammonium bromide, tetrabutylammonium iodide, methyltrioctylammonium chloride, tetraethylphosphonium bromide, and tetraethylphosphonium iodide.

11. The process according to claim 9 wherein the second catalyst is selected from the group consisting of tetrabutylammonium hydrogen sulfate, tetrabutylammonium halide, tetraethylammonium halide, methyltrioctylammonium chloride and tetraethylphosphonium halide.

12. The process according to claim 9 wherein the reaction of the intermediate is carried out in a solvent selected from the group consisting of aliphatic hydrocarbons, aromatic hydrocarbons and chlorohydrocarbons.

\* \* \* \* \*